US00PP36509P2

(12) United States Plant Patent
van Dijk

(10) Patent No.: US PP36,509 P2
(45) Date of Patent: Feb. 25, 2025

(54) ***ANTHURIUM* PLANT NAMED 'AN2772113'**

(50) Latin Name: *Anthurium andreanum*
Varietal Denomination: AN2772113

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 18/791,389

(22) Filed: Jul. 31, 2024

(51) Int. Cl.
*A01H 5/02* (2018.01)
*A01H 6/10* (2018.01)

(52) U.S. Cl.
USPC ..... Plt./366

(58) Field of Classification Search
USPC ..... Plt./366, 365
CPC ..... A01H 5/02; A01H 5/00; A01H 6/10
See application file for complete search history.

(56) References Cited

U.S. PATENT DOCUMENTS

PP30,921 P2 * 10/2019 Van Dijk ..... A01H 6/00
Plt./366

* cited by examiner

*Primary Examiner* — June Hwu
(74) *Attorney, Agent, or Firm* — C. Anne Whealy

(57) ABSTRACT

A new and distinct cultivar of *Anthurium* plant named 'AN2772113', characterized by its upright to outwardly arching and uniform plant habit; freely clumping growth habit; bushy and dense plants; narrowly cordate dark green-colored leaves; freely flowering habit; inflorescences that are positioned within to slightly above the foliar plane on strong and mostly upright scapes; broadly cordate white-colored spathes and light orangish yellow-colored spadices; and durable spathes that impart good inflorescence longevity.

2 Drawing Sheets

Figure 1:
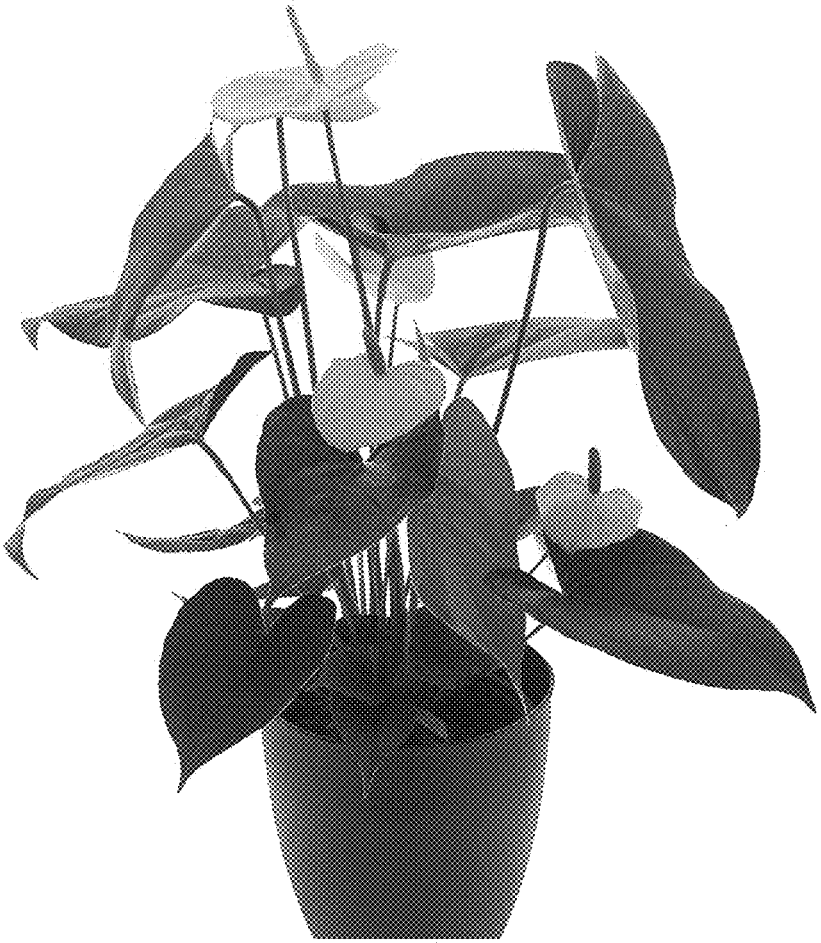

Botanical designation: *Anthurium andreanum.*
Cultivar denomination: 'AN2772113'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Anthura B.V. of Bleiswijk, The Netherlands on Nov. 22, 2023, application number 2023/2440. Foreign priority is not claimed to this application.

BACKGROUND OF THE INVENTION

The present invention relates to a new and distinct cultivar of *Anthurium* plant, botanically known as *Anthurium andreanum* and hereinafter referred to by the name 'AN2772113'.

The new *Anthurium* plant is a product of a controlled breeding program conducted by the Inventor in Bleiswijk, The Netherlands. The objective of the breeding program is to create new freely-clumping *Anthurium* plants with attractive white-colored, durable and glossy spathes.

The new *Anthurium* plant originated from a cross-pollination made by the Inventor in October, 2013 in Bleiswijk, The Netherlands of a proprietary selection of *Anthurium andreanum* identified as code number 10-020860-0002, not patented, as the female, or seed, parent with a proprietary selection of *Anthurium andreanum* identified as code number 10-024661-0005, not patented, as the male, or pollen, parent. The new *Anthurium* was discovered and selected by the Inventor as a single flowering plant within the progeny of the stated cross-pollination in a controlled greenhouse environment in Bleiswijk, The Netherlands in May, 2016.

Asexual reproduction of the new *Anthurium* plant by in vitro meristem propagation in a controlled environment in Bleiswijk, The Netherlands since August, 2018 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2772113'. These characteristics in combination distinguish 'AN2772113' as a new and distinct *Anthurium* plant:

1. Upright to outwardly arching and uniform plant habit.
2. Freely clumping growth habit; bushy and dense plants.
3. Narrowly cordate dark green-colored leaves.
4. Freely flowering habit.
5. Inflorescences that are positioned within to slightly above the foliar plane on strong and mostly upright scapes.
6. Broadly cordate white-colored spathes and light orangish yellow-colored spadices.
7. Durable spathes that impart good inflorescence longevity.

Plants of the new *Anthurium* differ primarily from plants of the female parent selection in the following characteristics:

1. Plants of the new *Anthurium* are not as freely clumping as plants of the female parent selection.
2. Spathes of plants of the new *Anthurium* are broadly cordate in shape whereas spathes of plants of the female parent selection are broadly ovate in shape.
3. Spadices of plants of the new *Anthurium* are not as tapering as spadices of plants of the female parent selection.

Plants of the new *Anthurium* differ primarily from plants of the male parent selection in the following characteristics:

1. Basal leaf lobes of plants of the new *Anthurium* are flat and separate whereas basal leaf lobes of plants of the male parent selection are incurved and close to imbricate.
2. Spathes of plants of the new *Anthurium* are more rugose than spathes of plants of the male parent selection.

Plants of the new *Anthurium* can also be compared to plants of *Anthurium andreanum* 'Anthfraxk', disclosed in U.S. Plant Pat. No. 30,921. In side-by-side comparisons, plants of the new *Anthurium* differ primarily from plants of 'Anthfraxk' in the following characteristics:

1. Basal leaf lobes of plants of the new *Anthurium* are flat and separate whereas basal leaf lobes of plants of 'Anthfraxk' are incurved and close to imbricate.
2. Spathes of plants of the new *Anthurium* are glossier than spathes of plants of 'Anthfraxk'.
3. Spadices of plants of the new *Anthurium* are not as tapering as spadices of plants of 'Anthfraxk'.

BRIEF DESCRIPTION OF THE PHOTOGRAPHS

The accompanying photographs illustrate the overall appearance of the new *Anthurium*. The photographs show the colors as true as it is reasonably possible to obtain in colored reproductions of this type. Colors in the photographs may differ slightly from the color values cited in the detailed botanical description which accurately describe the colors of the new *Anthurium*.

The photograph on the first sheet (FIG. 1) is a side perspective view of a typical plant of 'AN2772113' grown in a container.

Figure 2:
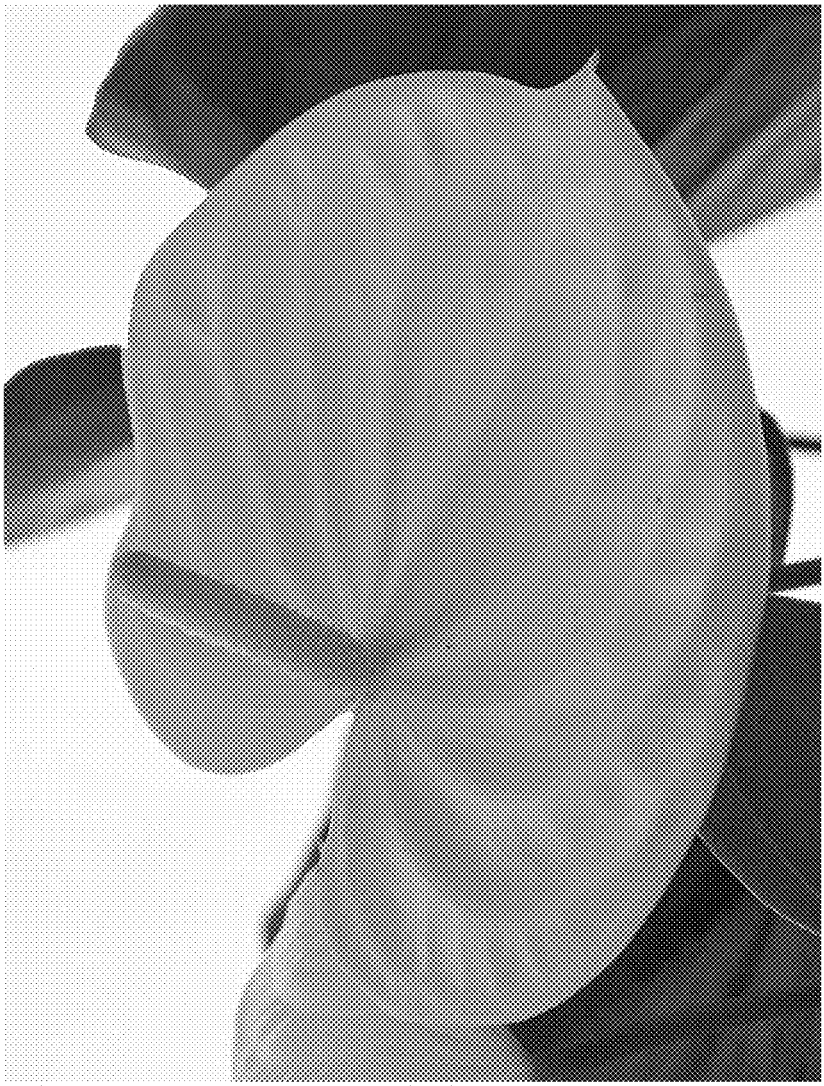

The photograph on the second sheet (FIG. 2) is a close-up view of a typical inflorescence of 'AN2772113'.

DETAILED BOTANICAL DESCRIPTION

The aforementioned photographs and following observations and measurements describe plants grown in 17-cm containers during the late winter in a glass-covered greenhouse in Bleiswijk, The Netherlands. Plants were grown under conditions and practices which approximate those generally used in commercial *Anthurium* production. During the production of the plants, day and night temperatures ranged from about 19° C. to 22.5° C. and light levels ranged from 100 μmol to 200 μmol. Plants were twelve months old when the photographs and the detailed description were taken. In the following description, color references are made to The Royal Horticultural Society Colour Chart, 2015 Edition, except where general terms of ordinary dictionary significance are used.

Botanical classification: *Anthurium andreanum* 'AN2772113'.

Parentage:

*Female, or seed, parent*.—Proprietary selection of *Anthurium andreanum* identified as code number 10-020860-0002, not patented.

*Male, or pollen, parent*.—Proprietary selection of *Anthurium andreanum* identified as code number 10-024661-0005, not patented.

Propagation:

*Type*.—By in vitro meristem propagation.

*Time to initiate roots, summer and winter*.—About two weeks at temperatures about 19° C. to 22.5° C.

*Time to produce a rooted young plant, summer and winter*.—About six to eight weeks at temperatures about 19° C. to 22.5° C.

*Root description*.—Medium in thickness, fibrous; typically creamy white slightly tinged with pink in color, actual color of the roots is dependent on substrate composition, water quality, fertilizer type and formulation, substrate temperature and physiological age of roots.

*Rooting habit*.—Freely branching, medium density.

Plant description:

*Plant shape*.—Upright to outwardly spreading and uniform plant habit; overall shape, roughly spherical.

*Growth habit*.—Freely clumping habit with about four clumps developing per plant imparting a bushy and dense appearance; moderately vigorous growth habit and moderate growth rate.

*Plant height, from soil level to top of leaf plane*.—About 40.7 cm.

*Plant height, from soil level to top of inflorescences*.—About 42.8 cm.

*Plant diameter or spread*.—About 50 cm.

Leaf description:

*Arrangement*.—Alternate; simple; about four leaves per clump.

*Length*.—About 26.1 cm.

*Width*.—About 15.5 cm.

*Shape*.—Narrowly cordate.

*Apex*.—Apiculate with a short mucronate tip.

*Base*.—Cordate; basal lobes free.

*Margin*.—Entire; slightly and coarsely undulate.

*Texture and luster, upper and lower surfaces*.—Smooth, glabrous; moderately leathery; glossy.

*Venation pattern*.—Pinnate.

*Color*.—Developing leaves, upper surface: Close to 143A. Developing leaves, lower surface: Close to a blend of 143A and 144A. Fully expanded leaves, upper surface: Close to a blend of 139A and 147A; narrow marginal edges, close to 144B; venation, close to 143B. Fully expanded leaves, lower surface: Close to a blend of 143A and 144A; venation, close to N144B.

*Petioles*.—Length: About 28.2 cm. Diameter: Distally, about 3.5 mm; proximally, about 5 mm. Strength: Strong. Texture and luster, upper and lower surfaces: Smooth, glabrous; slightly glossy. Color, upper surface: Close to a blend of 143A and 144A. Color, lower surface: Close to 144A. Geniculum length: About 2.2 cm. Geniculum diameter: About 4 mm by 5.5 mm. Geniculum texture, upper and lower surfaces: Smooth, glabrous. Geniculum color, upper surface: Close to 144A. Geniculum color, lower surface: Close to a blend of 144B and 146D. Wing length: About 2.8 cm. Wing diameter: About 5 mm. Wing color: Close to 144B.

Inflorescence description:

*Inflorescence arrangement and flowering habit.*—Spathes with spadices held within and slightly above the foliar plane on strong and erect scapes; flowering structures arise from leaf axils; freely and continuous flowering year-round in controlled temperature greenhouses in The Netherlands; typically about seven developing and developed inflorescences per plant at one time; inflorescence development commences about 2.5 to 3.5 months after planting.

*Inflorescence longevity.*—Depending on temperature, spathes maintain good substance for about two months on the plant; inflorescences persistent.

*Fragrance.*—None detected.

*Spathes.*—Length: About 9.3 cm. Width: About 10.1 cm. Shape: Broadly cordate; typically flat to slightly concave to slightly convex. Apex: Abruptly and broadly acute with a mucronate tip. Base: Cordate. Margin: Entire; slightly and coarsely undulate. Aspect: At about 100° from the scape axis. Texture and luster, upper and lower surfaces: Smooth, glabrous; moderately leathery; rugose; glossy. Color: When developing, front surface: Close to NN155A; at the apex, close to 155A and 155B. When developing, rear surface: Close to 155C; at the apex, close to 155B; towards the base, slightly tinged and veined with close to 145B. Fully developed, front surface: Close to NN155A; at the apex, close to 155A and 155B; with subsequent development, at the apex, close to 145A and 145B and towards the base, close to 144A to 144C. Fully developed, rear surface: Close to 155C; at the apex, close to 155B; towards the base, slightly tinged and veined with close to 145A and 145B; with subsequent development, color becoming closer to 155B and 155C, at the apex, close to 144A and 144B and towards the base, tinged and veined with close to 143A to 143C.

*Spadices.*—Length: About 4.1 cm. Diameter: About 7 mm. Shape: Columnar, slightly tapering towards the apex; apex, obtuse; base, obtuse; in cross-section, rounded. Aspect: About 80° from the spathe axis and about 15° from the scape axis. Color: Immature: Close to a blend of 16C and 162B and distally, close to 154C. Mature: Close to 159B and distally, close to 14C. Flowers: Type: Hermaphroditic. Quantity per spadix: Numerous, about 200. Height: About 0.5 mm. Diameter: About 2 mm. Shape: Roughly square. Anther color: Close to 159B. Pollen amount: Moderate. Pollen color: Close to 158C. Stigma color: Close to 159C to 159D.

*Scapes.*—Length: About 32.5 cm. Diameter: About 4 mm. Strength: Strong. Aspect: About 10° from vertical. Color: Close to 144A.

*Seed and fruit.*—To date, seed and fruit development has not been observed on plants of the new *Anthurium.*

Pathogen & pest resistance: To date, plants of the new *Anthurium* have not been observed to be resistant to pathogens or pests common to *Anthurium* plants.

Temperature tolerance: Plants of the new *Anthurium* have been observed to be tolerant to high temperatures about 30° C. and to be hardy to USDA Hardiness Zone 10.

It is claimed:

1. A new and distinct *Anthurium* plant named 'AN2772113' as herein illustrated and described.

* * * * *